(12) United States Patent
McDonough et al.

(10) Patent No.: US 8,946,200 B2
(45) Date of Patent: Feb. 3, 2015

(54) PHARMACEUTICALLY ACTIVE NANOSUSPENSIONS

(75) Inventors: Joseph A McDonough, Helotes, TX (US); Hong Dixon, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 1175 days.

(21) Appl. No.: 11/555,995

(22) Filed: Nov. 2, 2006

(65) Prior Publication Data

US 2008/0107736 A1    May 8, 2008

(51) Int. Cl.
  *A01N 43/00*  (2006.01)
  *A61K 31/33*  (2006.01)
  *B29B 9/00*   (2006.01)
  *A61K 31/57*  (2006.01)
  *A61K 9/14*   (2006.01)

(52) U.S. Cl.
  CPC .. *A61K 31/57* (2013.01); *A61K 9/14* (2013.01)
  USPC .............................................. 514/183; 264/5

(58) Field of Classification Search
  None
  See application file for complete search history.

(56) References Cited

U.S. PATENT DOCUMENTS

| | | |
|---|---|---|
| 2,305,947 A | 8/1942 | Armstrong et al. |
| 2,305,917 A | 12/1942 | Armstrong |
| 2,816,113 A | 12/1957 | Wilson |
| 3,135,761 A | 6/1964 | Hackley et al. |
| 3,137,702 A | 6/1964 | Luttringhaus |
| 3,629,425 A | 12/1971 | Hussain |
| 3,929,813 A | 12/1975 | Higuchi et al. |
| 4,128,651 A | 12/1978 | Hagedorn |
| 4,305,947 A | 12/1981 | Bartner |
| 4,540,602 A * | 9/1985 | Motoyama et al. ...... 427/213.31 |
| 4,705,777 A | 11/1987 | Lehrer et al. |
| 4,880,610 A | 11/1989 | Constantz |
| 5,130,438 A | 7/1992 | Hsiao et al. |
| 5,145,684 A | 9/1992 | Liversidge et al. |
| 5,298,504 A | 3/1994 | Sommer et al. |
| 5,589,167 A | 12/1996 | Cleland |
| 5,662,883 A | 9/1997 | Bagchi et al. |
| 5,716,642 A | 2/1998 | Bagchi et al. |
| 5,770,181 A | 6/1998 | Kirkland |
| 5,902,816 A | 5/1999 | Viner |
| 5,929,093 A | 7/1999 | Pang et al. |
| 6,007,845 A | 12/1999 | Domb et al. |
| 6,117,454 A | 9/2000 | Kreuter et al. |
| 6,355,271 B1 | 3/2002 | Bell et al. |
| 6,395,029 B1 | 5/2002 | Levy et al. |
| 6,656,505 B2 | 12/2003 | Kundu et al. |
| 6,815,543 B1 * | 11/2004 | Bernardelli .................. 540/145 |
| 6,861,068 B2 | 3/2005 | Ng et al. |
| 6,881,745 B2 | 4/2005 | Hayes et al. |
| 7,037,528 B2 | 5/2006 | Kipp et al. |
| 7,081,161 B2 | 7/2006 | Genge et al. |
| 7,282,194 B2 | 10/2007 | Sung et al. |
| 7,300,670 B2 | 11/2007 | Venus et al. |
| 7,387,792 B2 | 6/2008 | Hirsh et al. |
| 7,390,384 B2 | 6/2008 | Fang et al. |
| 8,309,134 B2 | 11/2012 | McDonough et al. |
| 8,404,850 B2 | 3/2013 | Cabell et al. |
| 8,722,706 B2 | 5/2014 | Dixon et al. |
| 2003/0073619 A1 | 4/2003 | Mahato et al. |
| 2004/0022820 A1 | 2/2004 | Anderson |
| 2004/0256749 A1 * | 12/2004 | Chaubal et al. ................. 264/5 |
| 2004/0266890 A1 * | 12/2004 | Kipp et al. ..................... 516/20 |
| 2005/0106257 A1 | 5/2005 | Albayrak |
| 2005/0113489 A1 | 5/2005 | Baran, Jr. et al. |
| 2005/0118108 A1 * | 6/2005 | Cowan et al. ................... 424/45 |
| 2005/0220888 A1 | 10/2005 | Putcha et al. |
| 2006/0063662 A1 | 3/2006 | Hata et al. |
| 2006/0183777 A1 | 8/2006 | Huang et al. |
| 2006/0216353 A1 * | 9/2006 | Liversidge et al. .......... 424/489 |
| 2007/0093518 A1 | 4/2007 | Wetherell et al. |
| 2007/0134339 A1 | 6/2007 | Jenkins et al. |
| 2007/0190160 A1 | 8/2007 | Turos et al. |
| 2008/0145439 A1 | 6/2008 | Lobl et al. |
| 2008/0241256 A1 | 10/2008 | Kuhn |
| 2009/0263491 A1 | 10/2009 | Kreuter et al. |
| 2009/0281144 A1 | 11/2009 | Cabell et al. |
| 2009/0304720 A1 | 12/2009 | Kreuter et al. |
| 2010/0040692 A1 | 2/2010 | Dixon et al. |
| 2010/0086601 A1 | 4/2010 | McDonough et al. |
| 2011/0195125 A1 | 8/2011 | McDonough et al. |

FOREIGN PATENT DOCUMENTS

| | | | |
|---|---|---|---|
| EP | 1319400 | 6/2003 | |
| WO | 9814587 | 4/1998 | |
| WO | 9841188 | 9/1998 | |
| WO | WO01/63362 A2 * | 8/2001 | ............... G03F 7/00 |
| WO | 0232402 | 4/2002 | |
| WO | 2004073033 A2 | 8/2004 | |
| WO | 2005/123581 A1 | 12/2005 | |
| WO | 2007/001355 A2 | 1/2007 | |
| WO | 2007/084460 A2 | 7/2007 | |
| WO | 2009114298 | 9/2009 | |
| WO | 2010019398 A1 | 2/2010 | |
| WO | 2010040057 A1 | 4/2010 | |

OTHER PUBLICATIONS

Dennison et al (British Medical Journal, vol. 316, pp. 789-790; 1998).*
Farcasiu et al (Catalysis Letters, vol. 31, pp. 351-358; 1995).*
Kenalog (triamcinolone acetonide) Ointment [online], www.dailymed.nlm.nh.gov, Jan. 2006 [retrieved on Jun. 21, 2008]. Retrieved from the Internet: <URL: http://dailymed.nlm.nih.gov/dailymed/fda/fdaDrugXsl.cfm?id=1872&type=display.*

(Continued)

*Primary Examiner* — Jason Sims
*Assistant Examiner* — Tori M Strong
(74) *Attorney, Agent, or Firm* — Grossman, Tucker et al

(57) ABSTRACT

The present disclosure is directed at a pharmaceutically active nanoparticle suspension that may be optically clear. Such suspensions may be formed by selective dissolution of a pharmaceutically active compound in a first solvent followed by introduction into a second solvent, such as an aqueous medium, without substantial use of surfactants and/or mechanical shear.

15 Claims, 2 Drawing Sheets

(56) References Cited

OTHER PUBLICATIONS

Patani et al. (Chem. Rev., vol. 96, No. 8, pp. 3147-3176; 1996).*
Giuliani et al. (Optical and Quantum Electronics, vol. 9, pp. 263-264; 1977).*
Chemistry and Industry; Applied Chemistry; Nigel Freestone; Nov. 7, 2005 (4 pgs).
Chemistry and Industry; New Drug Delivery Systems; Alexander T. Florence; Dec. 20, 1993 (7 pgs).
Advanstar Communications, Inc.; Pharmaceutical Technology; Vivek Kharb; Meenakshi Bhatia; Harish Dureja; Deepak Kaushik; Feb. 1, 2006 (11 pgs).
Advanstar Communications, Inc.; Pharmaceutical Technology Europe; Magdalene Radtke; Eliana B. Souto; Rainer H. Muller; Apr. 1, 2005 (4 pgs).
Radic, et al., "Evaluation of HI-6 oxime: potential use in protection of human acetylcholinesterase inhibited by antineoplastic drug irinotecan and its cyto/genotoxicity in vitro," Acta Biochimica Polonica vol. 54 No. 3/2007, 583-593, Aug. 23, 2007.
Stojiljkovic, et al., "Pryidinum Oximes: Rationale for their Selection as casual Antidotes against Organophosphate Poisonings and current solutions for auto-injectors," Arh Hig Toksikol 2006, 57:435-443.
International Search Report and Written Opinion of the ISA issued in PCT/US09/35539 dated Jul. 17, 2009 (8 pgs).
International Search Report and Written Opinion of the ISA issued in PCT/US09/52457 dated Oct. 6, 2009 (9 pgs).
Luo et al, "An In Vitro Comparative Study on the Reactivation of Nerve Agent-Inhibited Guinea Pig and Human Acetylcholinesterases by Oximes"; Biochemistry 2007, 46, pp. 11771-11779.
Garcia et al, "Sensitive and Rapid Blood and Tissue HPLC Oxime Assay and Pharmacokinetics of MMB-4 in Guinea Pigs and African Green Monkeys"; Walter Reed Army Institute of Research, Nov. 1, 2006, (8 pgs).
Antonijevic et al., "Unequal Efficacy of Pyridinium Oximes in Acute Organophosphate Poisoning," Clinical Medicine & Research, vol. 5, No. 1:71-82.
Praetorius, et al., "Engineered Nanoparticles in Cancer Therapy," Recent Patents on Drug Delivery & Formation 2007,vol. 1 No. 1, pp. 37-51.
BIOSANTE Pharmaceuticals, "Hormone Therapy—A Multi-Billion Dollar Market," Investor Fact Sheet Sep. 2007; www.biosantepharma.com; (2 pages).
T.Welzel, et al., "Transfection of Cells With Custom-made Calcium Phosphate Nanoparticles Coated With DNA"; The Royal Society of Chemistry 2004; J. Mater. Chem. 2004, 14, pp. 2213-2217.
S. Bisht, et al., "pDNA Loaded Calcium Phosphate Nanoparticles: Highly Efficient Non-Viral Vector for Gene Delivery"; International Journal of Pharmaceutics 288 (2005), pp. 157-168.
T.Liu, et al., "Calcium Phosphate Nanoparticles as a Novel Nonviral Vector for Efficient Transfection of DNA in Cancer Gene Therapy"; Cancer Biotherapy & Radiopharmaceuticls, vol. 20, No. 2, 2005, pp. 141-150.
A. Brioschi, et al, "Solid Lipid Nanoparticles: Could They Help . . . "; Neurological Research 2007, vol. 29, Apr. 2007; pp. 324-330.
M. Nahar, et al, "Functional Polymeric Nanoparticles: An Efficient . . . "; Critical Reviews™ In Therapeutic Drug Carrier Systems, 23(4):259-318 (2006); Begell House Inc., http://begellhouse.com; downloaded Sep. 18, 2009 from IP 129.162.1.41 by Celia Frausto.
International Search Report and Written Opinion dated Nov. 23, 2009 issued in related International Patent Application No. PCT/US0959386.
DiGiovanni, JR., M.D., Cleto, Domestic Terrorism With Chemical or Biological Agents: Psychiatric Aspects, Am J Psychiatry, Oct. 1999, pp. 1500-1505, vol. 156:10.
D'Mello, G.D., Behavioural Toxicity of Anticholinesterases in Humans and Animals—A Review, Human & Experimental Toxicology, 1993, pp. 3-7, vol. 12.
Eyer, et al., Oximes—Chapter 15, Chemical Warfare Agents: Toxicology and Treatment, 2007, pp. 305-329, 2nd Edition.

Jager, et al., Toxicity of Diacetyl Monoxime and of Pyridine-2-Aldoxime Methiodide in Man, Bull John Hopkins Hosp., 1958, pp. 203-211, vol. 102.
Jamal, Goran A., Long term neurotoxic effects of organophosphate compounds, Adverse Drug React. Toxicol. Rev, 1995, pp. 85-99, vol. 14(2).
Marrs et al., Chemical Warfare Agents: Toxicology and Treatment Second Edition, 2007, pp all. Table of contents attached electronically, physical book is cited and supplied in U.S. Appl. No. 12/702,095 which was mailed to USPTO Oct. 8, 2010.
McDonough, et al., Behavioral Correlates of Soman-Induced Neuropathology: Deficits in DRL Acquisition, Neurobehavioral Toxicology and Teratology, 1986, pp. 179-187, vol. 8.
Luo, et al., "Development of a broad-spectrum Oxime for the treatment of nerve agent toxicity," Conference paper, Division of Biochemistry, Walter Reed Army Institute of Research, Silver Spring, MD 20910, Report Date: Nov. 2006 Report No. A376184. Available at http://www.dtic.mil/cgi-bin/GetTRDoc?Location=U2&doc=GetTRDoc.pdf&AD=ADA481673, retrieved on Mar. 9, 2011.
U.S. Office Action dated Mar. 11, 2011 issued in related U.S. Appl. No. 12/245,450.
U.S. Office Action dated May 25, 2011 issued in related U.S. Appl. No. 12/192,400.
Munavalli, et al; Preparation and Properties of Methylenebispyridinium Derivatives; Heterocycles 1986, vol. 24. No. 7; pp. 1883-1892.
U.S. Office Action mailing dated Jun. 22, 2011 issued in related U.S. Appl. No. 12/047,988.
European Supplementary Search Report—mailing date Sep. 27, 2011, issued in related European Appln. No. 09718843.7.
Sevelova et al, "Antidotal Treatment of GF-agent intoxication in mice with bispyridinium Oximes", Toxicology, vol. 207, No. 1, pp. 1-6, 2005.
Aurbek et al, "Analysis of Inhibition, Reactivation and Aging Kinetics of Highly Toxic Organophosphorus Compounds with Human and Pig Acetylcholinesterase", Toxicology, vol. 224, No. 1-2. pp. 91-99, 2006.
Office Action dated Dec. 29, 2011 issued in related U.S. Appl. No. 12/047,988.
Office Action dated Nov. 29, 2011 issued in related U.S. Appl. No. 12/245,450.
Office Action dated Jan. 26, 2012 issued in related U.S. Appl. No. 12/192,400.
Office Action dated Jan. 5, 2012 issued in related U.S. Appl. No. 12/702,095.
European Search Report dated Oct. 31, 2011 issued in related European Patent Application No. 09807064.2.
Bagryanskaya, et al., "Study of alkaloids from the flora of the Siberian and Altai regions. 6.* Crystal and molecular structure of songorine Z-oxime," Russian Chemical Bulletin, International Edition, vol. 50, No. 11, pp. 2092-2094, Nov. 2001.
Gao, et al., "Influence of particle size on transport of methotrexate across blood brain barrier by polysorbate 80-coated polybutylcyanoacrylate nanoparticles," International Journal of Pharmaceutics 310 (2006) 213-219.
Hobbiger, et al., "Reactivation of Phosphorylated Acetocholinesterases by Pyridinium Aldoximes and Related Compounds," Biochem J. May 1960; 75(2): 363-372.
Kuca, et al., "Effective bisquaternary reactivators of tabun-inhibited AChE," J. Appl. ToxiCol. 2005; 25: 491-495.
Liu, et al., "Biologically active core/shell nanoparticles self-assembled from cholesterol-terminated PEG-TAT for drug delivery across the blood-brain barrier," Biomaterials 29 (2008) 1509-1517.
Macauley, et al., Chromatographic separation and NMR characterization of the isomers of MMB-4 a bis-(pyridiniumaldoxime), Journal of Pharmaceutical and Biomedical Analysis 49 (2009) 889-894.
Thiermann, "HI 6 dimethanesulfonate has better dissolution properties than HI 6 dichloride for application in dry/wet autoinjectors," International Journal of Pharmaceutics vol. 137, Issue 2, Jun. 28, 1996, pp. 167-176.
Wu, et al., "Blood-Brain Barrier Transport of Reduced Folic Acid," Pharm Res. Mar. 1999;16(3):415-9.

(56) References Cited

OTHER PUBLICATIONS

Office Action dated Sep. 14, 2012 issued in related U.S. Appl. No. 12/047,988.
Office Action dated Sep. 27, 2012 issued in related U.S. Appl. No. 12/702,095.
Office Action dated Oct. 11, 2012 issued in related U.S. Appl. No. 12/192,400.
Chaumeil; "Micronization: A Method of Improving the Bioavailability of Poorly Soluble Drugs"; Methods and Findings in Experimental and Clinical Pharmacology, Apr. 1998, vol. 20 (3): pp. 211-215; Copyright 1998 Prous Science, CCC: 0379-0355/98.
Garner, et al; Comparison of the Absorption of Micronized (Daflon 500 mg) and Nonmicronized 14 C-Diosmin Tablets After Oral Administration to Healthy Volunteers by Accelerator Mass Spectrometry and Liquid Scintillation Counting; Journal of Pharmaceutical Sciences, vol. 91, No. 1, Jan. 2002, pp. 32-40.
Choi, et al; Amorphous Ultrafine Particle Preparation for Improvement of Bioavailability of Insoluble Drugs: Grinding Characteristics of Fine Grinding Mills; Elsevier, International Journal of Mineral Processing, vol. 74, Supplement 1, Dec. 2004, pp. S165-S172.
Gelperina, et al., "Drug delivery to the brain using surfactant-coated poly(lactide-co-glycolide) nanoparticles: Influence of the formulation parameters," European Journal of Pharmaceutics and Biopharmaceutics (2009) doi:10.1016/j.ejpb.2009.09.003.
Kurakhmaeva, et al., "Brain targeting of nerve growth factor using poly(butyl cyanoacrylate) nanoparticles," Journal of Drug Targeting, 2009; 17(8): 564-574.
Hekmatara, et al., "Efficient systemic therapy of rat glioblastoma by nanoparticle-bound doxorubicin is due to antiangiogenic effects," Clinical Neuropathology, vol. 28—No. 3/2009 (153-164).
Zensi, et al., "Albumin nanoparticles targeted with Apo E enter the CNS by transcytosis and are delivered to neurones," Journal of Controlled Release 137 (2009) 78-86.
Ulbrich, et al., "Transferrin- and transferrin-receptor-antibody-modified nanoparticles enable drug delivery across the blood-brain barrier (BBB)," European Journal of Pharmaceutics and Biopharmaceutics 71 (2009) 251-256.
Pereverzeva, et al., "Intravenous tolerance of a nanoparticle-based formulation of doxorubicin in healthy rats," Toxicology Letters 178 (2008) 9-19.
Kreuter, et al., "Use of nanoparticles for cerebral cancer," Tumori: 9-4: 271-277, 2008.
Kreuter, "Nanoparticles—a historical perspective," International Journal of Pharmaceutics 331 (2007) 1-10.
Petri, et al., "Mechanism of Action and Surfactant Influence During Chemotherapy of Brain Tumour Using Doxorubicin-Loaded Poly(butyl Cyanoacrylate) Nanoparticles," NSTI-Nanotech 2007, vol. 2, 2007, p. 386-389.
Ambruosi, et al., "Influence of surfactants, polymer and doxorubicin loading on the anti-tumour effect of poly(butyl cyanoacrylate) nanoparticles in a rat glioma model," Journal of Microencapsulation, Aug. 2006; 23(5): 582-592.
Ambruosi, et al., "Biodistribution of polysorbate 80-coated doxorubicin-loaded [14C]-poly(butyl cyanoacrylate) nanoparticles after intravenous administration to glioblastoma-bearing rats," Journal of Drug Testing, Feb. 2006; 14(2): 97-105.
Ambruosi, et al., "Body distribution of polysorbate-80 and doxorubicin-loaded [14C]-(poly(butyl cyanoacrylate) nanoparticles after i.v. administration in rats," Journal of Drug Targeting, Dec. 2005; 13(10): 535-542.
Schuller et al., "Degradation of microvascular brain endothelial cell β-catenin after co-culture with activated neutrophils from patients undergoing cardiac surgery with prolonged cardiopulmonary bypass," Biochemical and Biophysical Research Communications 329 (2005) 616-623.
Kreuter, "Application of nanoparticles for the delivery of drugs to the brain," International Congress Series 1277 (2005) 85-94.
Kreuter, "Influence of the Surface Properties on Nanoparticle-Mediated Transport of Drugs to the Brain," Journal of Nanoscience and Nanotechnology, 2004, vol. 4, No. 5; p. 484-488.
Kreuter, "Direct Evidence that Polysorbate-80-Coated Poly(Butylcyanoacrylate) Nanoparticles Deliver Drugs to the CNS via Specific Mechanisms Requiring Prior Binding of Drug to the Nanoparticles," Pharmaceutical Research, vol. 20, No. 3, Mar. 2003; p. 409-416.
Kreuter, "Transport of Drugs Across the Blood-Brain Barrier by Nanoparticles," Curr. Med. Chem.—Central Nervous System Agents, 2002, 2, 241-249.
Kreuter, et al. "Apolipoprotein-mediated Transport of Nanoparticle-bound Drugs Across the Blood-Brain Barrier," Journal of Drug Testing, 2002 vol. 10 (4), pp. 317-325.
Gelperina, et al., "Toxicological studies of doxorubicin bound to polysorbate 80-coated poly(butyl cyanoacrykate) nanoparticles in healthy rats and rats with intracranial glioblastoma," Toxicology Letters 126 (2002) 131-141.
Kreuter, "Nanoparticulate systems for brain delivery of drugs," Advanced Drug Delivery Reviews 47 (2001) 65-81.
Ramge, et al., "Polysorbate-80 coating enhances uptake of polybutylcyanoacrylate (PBCA)-nanoparticles by human and bovine primary brain capillary endothelial cells," European Journal of Neuroscience, vol. 12, pp. 1931-1940 (2000).
Ramge, et al., "Circadian Phase-dependent Antinociceptive Reaction in Mice and the Tail-flick Test after Intravenous Injection of Dalargin-Loaded Nanoparticles," Chronobiology International, 16(6), 767-777 (1999).
Alyautdin, et al., "Drug delivery to brain by nanoparticles," (2003) eksperimental'naya i Klinicheskaya Farmakologiya, 66 (2), pp. 65-68.
Balali-Mood MD PHD, et al., "Neurotoxic Disorders of Organophosphorous Compounds and Their Managements," Arch Iranian Med 2008; 11 (1): 65-89.
Kuca, et al., "Preparation of Oxime HI-6 (Dichloride and Dimethanesulphonate)—Antidote against Nerve Agents," Defense Science Journal, vol. 58, No. 3, May 2008, pp. 399-404.
Kuca, et al., "In Vitro Reactivation Potency of Acetylcholinesterase Reactivators—K074 and K075—to Reactivate Tabun-inhibited Human Brain Cholinesterases," Neurotoxicity Research, 2007, vol. 11(2), pp. 101-106.

* cited by examiner

PHARMACEUTICALLY ACTIVE NANOSUSPENSIONS

FIELD OF THE INVENTION

The present disclosure relates to pharmaceutically active nanoparticle suspensions. In particular, the present disclosure relates to a process for the preparation of pharmaceutically active and optically clear nanosuspension by selective dissolution of a pharmaceutically active compound in a first solvent followed by introduction into a second solvent, such as an aqueous medium, without substantial use of surfactants and/or mechanical shear.

BACKGROUND

Pharmaceutically active compounds, such as corticosteroids, may be understood as steroids produced by the adrenal cortex. Triamcinolone (TCO) is a synthetic corticosteroid that may be used to treat certain conditions such as inflammatory response due to retinal reattachment surgery. It may also be used to treat certain forms of arthritis, skin, blood, kidney, eye, thyroid and intestinal disorders, severe allergies, and asthma. TCO may be administered orally, by injection, inhalation or as a topical cream. Triamcinolone and other assorted pharmaceutically active compounds may exhibit poor solubility in aqueous media. Poor solubility may generally be associated with poor bioavailability. Bioavailability may be understood as the rate and extent in which the pharmaceutically active compound, as a drug, is absorbed by the body in a physiologically active form. By reducing the particle size of a drug and increasing the surface area of a drug the rate of dissolution may be increased and therefore may also increase bioavailability.

SUMMARY OF THE INVENTION

In exemplary embodiment, the present disclosure provides a nanoparticulate suspension of a pharmaceutically active compound. The suspension may be formed by combining a pharmaceutically active compound in a first solvent which may then be introduced into a second solvent which may then promote active compound precipitation. The first and/or second solvents may be substantially free of surfactant. The nanoparticulate suspension may be optically clear and contain active compound particulate of a desired particle size and may also be prepared without the use of mechanical shearing.

DETAILED DESCRIPTION

Figure 1:
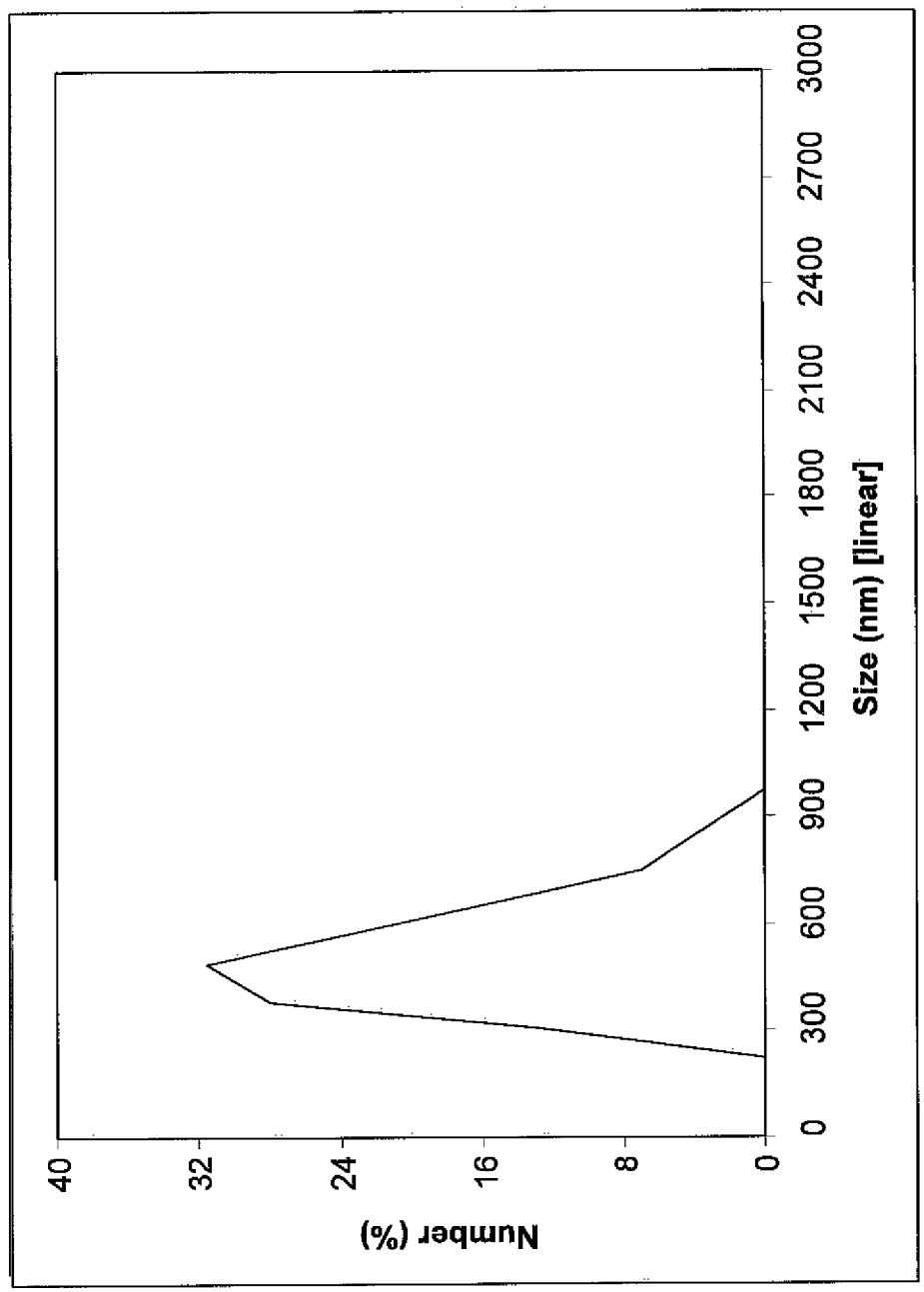
FIG. 1 illustrates one exemplary numerical particle size distribution of a nanoparticulate suspension.

The present disclosure relates to pharmaceutically active nanoparticle suspensions. A pharmaceutically active compound may be understood herein as a compound that exhibits biological activity, including nutritional, nutraceutical and/or pharmacological activity. The nanoparticle suspensions herein are contemplated for use as an injectable formulation, such as a formulation to inhibit inflammatory response, via techniques such as intravitreal administration. The nanoparticle suspensions are also contemplated for use in general drug delivery where increased bioavailability may be desired.

The nanoparticle suspension may include, as one example of a pharmaceutically active compound, a corticosteroid. The suspension may specifically include synthetic corticosteroid such as triamcinolone (TCO) represented by the following formula:

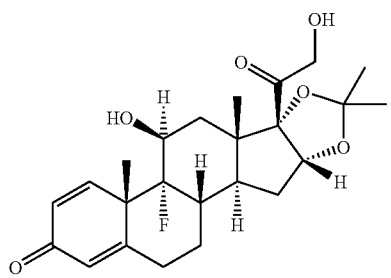

Other corticosteroids contemplated for use herein may include betamethasone, budesonide, cortisone, dexamethasone, cortisol, methylprednisolone, prednisone, prednisolone, etc.

The pharmaceutically active compound may be mixed with a first solvent, such as an organic solvent, which may specifically be a relatively polar solvent and/or which may be miscible with water to provide a single homogenous phase. Reference to polar solvent may be understood as an organic solvent containing one or more chemical functional groups (e.g., a hydroxyl group) in addition to carbon and hydrogen. As one representative example, the solvent may therefore include an organic alcohol, such as a secondary organic alcohol of the following general structure:

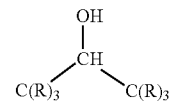

In the above general formula, the secondary alcohol may have one or a plurality of electron withdrawing R groups associated with the carbon atom(s) adjacent the hydroxyl group, such as halogens, carbonyl groups, nitrites, etc. Accordingly, an electron withdrawing group may be understood herein as any chemical functionality which may withdraw electrons and provide a relatively more acidic alcohol. In addition, as one or more R groups may comprise an electron-withdrawing group, the remaining R groups may include a hydrogen atom, an alkyl group, an aromatic group, a substituted alkyl group or a substituted aromatic group. The polar organic solvent may also be one that exhibits hydrogen bonding and is therefore capable of dissolving molecules with hydrogen bonding receptive sites such as oxygen, double bonds or amine groups.

In addition, the organic solvent herein may be separately characterized as having an acid ionization constant ($pK_a$) which may be understood as the propensity of the solvent to donate a proton in water at 25° C. Such $pK_a$ may be greater than or equal to about 7.0. The $pK_a$ may also fall in the range of about 7.0 and 14.0, including all values and incremental ranges therein, such as 9.0, 9.2, 9.4, 9.6, etc and/or 9.0-10.0, etc. One particularly suitable organic solvent may include hexafluoroisopropanol, $C_3H_2OF_6$ or HFIP, which may also be represented by the following general structural formula:

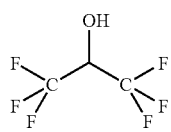

In one exemplary embodiment, the pharmaceutically active compound, such as a corticosteroid, may be present in the first solvent ($Sol_1$) such as HFIP at a ratio of less than about 2 mg of pharmaceutically active compound to at least 0.5 mL of HFIP, including all values and increments therein. For example, the pharmaceutically active compound may be present in the first solvent at the range of 0.001 to 1.99 mg to at least 0.5 mL of solvent, including all values and ranges therein. Accordingly, the pharmaceutically active compound may be prepared by forming a solution of about 1 mg of TCO in about 0.5 mL of HFIP. The solution of the pharmaceutically active compound and first solvent may then be added to a second solvent ($Sol_2$), such as an aqueous medium. It may also be appreciated that both the first solvent and/or second solvent are such that they do not substantially rely upon the use of surfactant (e.g. anionic, cationic or nonionic surfactants) or other related compounds having both hydrophobic and hydrophilic type functionality. That is, the solvents herein, which may be characterized as being substantially free of surfactants, may be understood as solvents in which surfactants are not relied upon to control and/or avoid particle aggregation. Accordingly, the level of surfactant herein may be at or less than about 1.0 pppm.

The second solvent may include an aqueous saline solution or a buffered saline solution such as phosphate buffered saline solution. Water, such as deionized water may also be employed which may be understood as water that lacks ions but which may contain other non-ionic type compounds. The pH of the aqueous medium may also be adjusted to approximately 6.0 to 9.0, including all increments and values therein, such as 7.4, 7.3, 8.0, etc. The organic solution of the pharmaceutically active compound and first solvent (e.g., 1 mg TCO/ 0.5 mL HFIP) may then be added to 2 mL or greater of the aqueous medium, including all values and increments therein to provide a nanoparticulate suspension or nanosuspension (i.e. precipitation of the pharmaceutically active compound). It may now therefore be appreciated that one non-limiting aspect of the method herein contemplates the combination of a relatively smaller amount of the first organic solvent with a relatively larger amount of the second aqueous based solvent, wherein as noted above, both solvents do not rely upon surfactants to regulate the potential for precipitated particle aggregation. In addition, it may be appreciated that the foregoing method does not rely upon the use of shearing to influence particle size formation within the nanosuspension, and in particular, the shearing procedure reported in U.S. Pat. No. 5,145,684. However, it may be appreciated that the nanoparticulate suspensions herein may utilize magnetic stirrers and other related techniques of stirring/agitation.

The nanosuspension formed herein may then be concentrated. For example, it may be concentrated to a ratio of 1 mg or less of pharmaceutically active compound to 1.25 mL or greater of first solvent and aqueous medium. Concentration may be performed by removing some of the aqueous medium and/or first solvent, via placement in a fume hood or by application of vacuum.

The particle size of the pharmaceutically active compound in the nanosuspension may be in the range of 100 nm to 1000 nm, including all values and increments therein, such as in the range of 250 nm to 1,000 nm, etc. Illustrated in FIG. 1 is an exemplary embodiment of a numerical particle size distribution of suspension of TCO in PBS having a pH of 7.4 and at a concentration of 0.5 mg/mL. As can be seen in FIG. 1 the number percent particle size may range from 250 nm to approximately 1000 nm. In addition, the highest relative number percent of particles fall in the range of about 450-525 nm. Such particle size determination may be accomplished on a Beckman Coulter PCS Submicron Particle Size Analyzer. Accordingly, a nanosuspension herein may be understood as any liquid medium containing pharmaceutically active compounds having particles with a size of less than or equal to about 1000 nm.

Figure 2:
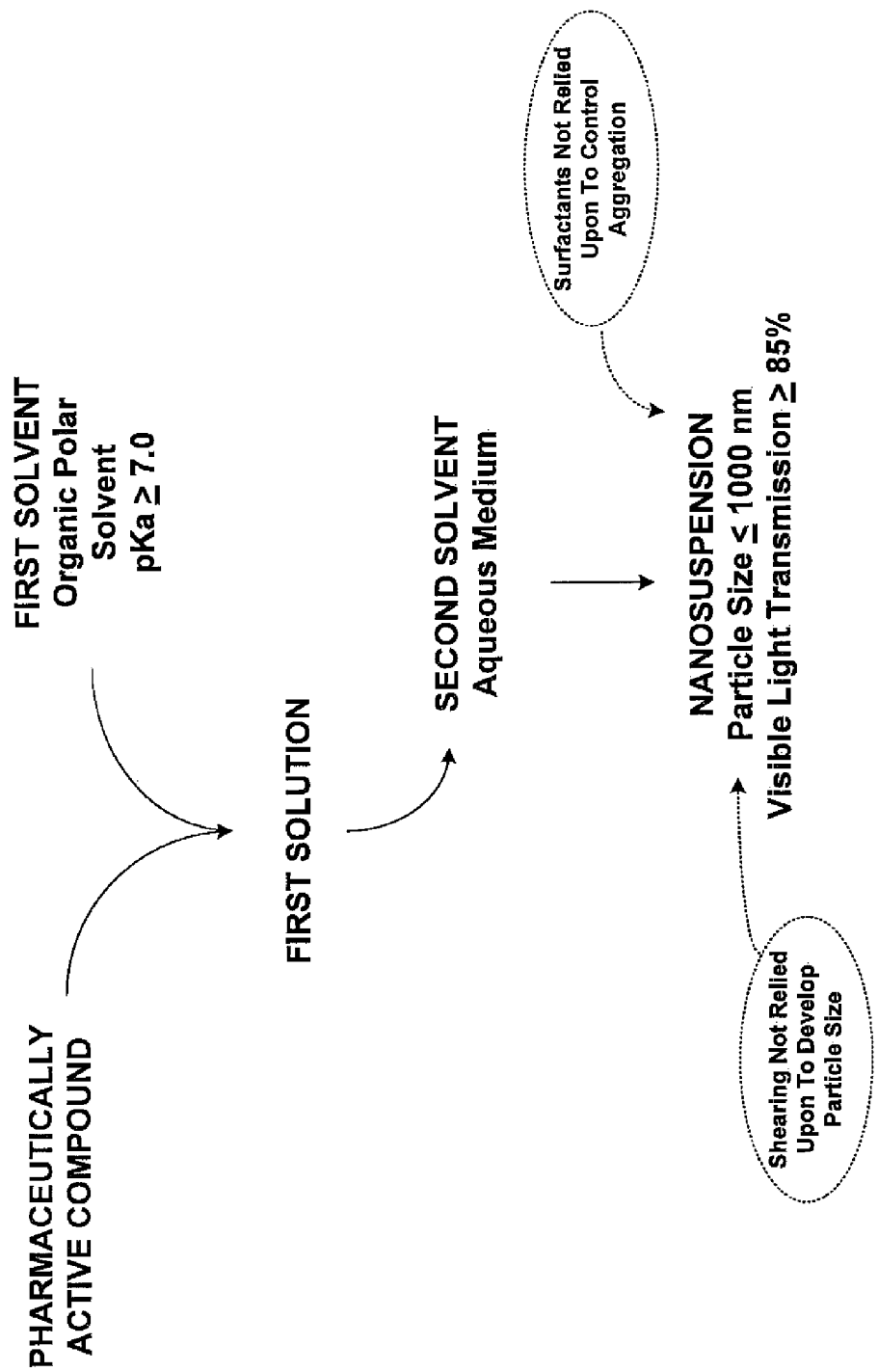
FIG. 2 diagrams one exemplary method for preparation of a nanoparticulate suspension.

The nanosuspensions formed herein may be optically clear or relatively transparent. This may be understood as a nanosuspension which is capable of transmitting about 85% or more visible light, including all values and increments therein. In addition, the nanosuspension may have a low refractive index in the range of 1.00 to 1.5 at a $\lambda$ of 598.3 nm, including all values and ranges therein, such as 1.0003, 1.33, etc. The refractive index of the material may be understood as the ratio of the velocity of electromagnetic radiation in the nanosuspension relative to its velocity in a vacuum. Accordingly, attention may now therefore be directed to FIG. 2 which illustrates in diagram format certain particular features of the present disclosure identified above as applied to the formation of a nanosuspension herein containing a pharmaceutically active compound.

In a further embodiment secondary pharmaceutically active compounds may be added to the nanosuspension to increase the activity, bioavailability or absorption rate of the primary pharmaceutically active compounds. These secondary compounds may include those which increase tissue permeability and may be considered spreading or diffusing substances, such as hyaluronidase. Hyaluronidase may be understood as any group of enzymes that catalyze the hydrolysis of certain complex carbohydrates, including hyaluronic acid, chondroitin sulfates, etc. By hydrolyzing hyaluronic acid, for example, the primary pharmaceutically active compound may diffuse more readily through the tissue.

The pharmaceutically active compound may also be microencapsulated, which may be understood as a process in which relatively small particles or droplets are surrounded by a coating to give relatively small capsules with many useful properties. For example, the micro-encapsulate may be a relatively small sphere or core with a uniform wall around the sphere, which may be a coating, shell or membrane. The micro-encapsulate may be in the range of a few micrometers to a few millimeters. The nanosuspension may be released from the microcapsule by rupture, dissolution of the wall, melting of the wall and diffusion through the wall. The wall may be formed of a biodegradable or non-biodegradable materials. Such biodegradable materials may include polyglycolic acid, polylactic acid, polylactic-co-glycolic acid, polycaprolactone, polyanhydrides, polyesters, etc. Non-biodegradable materials may include polyethylene, polypropylene, polyethylene-co-vinyl acetate, etc. The walls may be formed from a number of encapsulation processes such as coacervation, co-extrusion, interfacial polymerization, etc.

The following non-limiting examples provide further illustration regarding the formation of the pharmaceutically active nanosuspensions described herein.

EXAMPLE 1

A solution of TCO (1 mg) in hexafluoroisopropanol (HFIP) (0.5 mL) was prepared and added slowly into a magnetically stirred into phosphate buffered saline (PBS) (2 mL) having a pH of 7.4. The mixture was stirred uncovered in a fume hood for up to 24 hours. FIG. 1 illustrates the particle size distribution of suspension of TCO in pH 7.4 PBS at 0.5 mg/mL concentration. As illustrated in FIG. 1, the particles are smaller than approximately 1,000 nm. The clear nanoparticle suspension was further concentrated in a vacuum oven to about 1.5 mg/mL. However, a 1.0 mg/ML nanosuspension by precipitating 2 mg/0.5 mL TCO/HFIP into 2 mL PBS resulted in a cloudy solution, indicating microparticles were formed instead.

EXAMPLE 2

A solution of TCO (1 mg) in hexafluoroisopropanol (0.5 mL) was prepared and added slowly into a magnetically stirred deionized water (2 mL). The mixture was stirred uncovered in a fume hood for 3 hours and further concentrated in a vacuum oven. The nanoparticle suspension in deionized water, however, could only be concentrated to about 0.6 mg/mL of concentration before growing micron-sized crystals.

Although the illustrative embodiments of the present disclosure have been described above with reference to the accompanying drawings and examples, it is to be understood that the disclosure is not limited to those precise embodiments, and various changes and modifications may be affected therein by one skilled in the art. It is intended that such changes and modifications be included within the scope of the appended claims.

What is claimed is:

1. A method for preparing a nanoparticulate suspension of a pharmaceutically active compound comprising:
   combining a pharmaceutically active compound in a solvent to provide a solution of said pharmaceutically active compound at a concentration of 0.001 mg to 1.99 mg to 0.5 ml and wherein said solvent is an organic solvent having a pKa≥7.0;
   introducing said solution of said pharmaceutically active compound into an aqueous buffered solution and forming said nanoparticulate suspension of said pharmaceutically active compound by precipitation and without mechanical shearing under ambient conditions;
   wherein said suspension has a level of surfactant that is less than or equal to 1.0 ppm; and
   wherein said solvent consists essentially of an organic alcohol having the following structure:

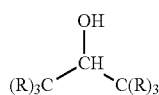

wherein one or more R groups are fluorine atoms and wherein the remaining R groups are independently selected from the group consisting of a hydrogen atom and an alkyl group.

2. The method of claim 1, wherein said nanoparticulate suspension has particles having sizes ≤1000 nm and said suspension is capable of transmitting≥85% visible light.

3. The method of claim 2, wherein said particle size is between 250 nm-1000 nm.

4. The method of claim 1, wherein said pharmaceutically active compound comprises a corticosteroid.

5. The method of claim 1, wherein said pharmaceutically active compound comprises triamcinolone, said solvent is hexafluoroisopropanol, and said buffered aqueous solution is a phosphate buffered saline.

6. A method for preparing a nanoparticulate suspension of a pharmaceutically active compound comprising:
   combining a pharmaceutically active compound in a solvent to provide a solution of said pharmaceutically active compound at a concentration of 0.001 mg to 1.99 mg to 0.5 ml and wherein said solvent is an organic solvent having a pKa≥7.0;
   introducing said solution containing said pharmaceutically active compound into deionized water and forming said nanoparticulate suspension of said pharmaceutically active compound by precipitation and without mechanical shearing under ambient conditions wherein said suspension has a level of surfactant that is less than or equal to 1.0 ppm;
   wherein said nanoparticulate suspension has particles having sizes≤1000 nm and said particle size is formed without mechanical shearing under ambient conditions; and
   wherein said solvent consist essentially of an organic alcohol having the following structure:

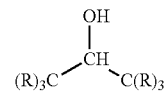

wherein one or more R groups are fluorine atoms and wherein the remaining R groups are independently selected from the group consisting of a hydrogen atom and an alkyl group.

7. The method of claim 6, wherein said pharmaceutically active compound comprises a corticosteroid.

8. The method of claim 6, wherein said pharmaceutically active compound comprises triamcinolone, said solvent is hexafluoroisopropanol.

9. A method for preparing a nanoparticulate suspension of a corticosteroid compound comprising:
   combining a corticosteroid in an organic solvent that is miscible with water to provide a solution of said corticosteroid, wherein said solvent has a pKa≥7.0 and consists essentially of the following structure:

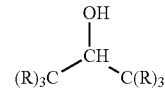

wherein one or more R groups are fluorine atoms, wherein the remaining R groups are selected from the group consisting of a hydrogen atom, and an alkyl group and wherein said corticosteroid is present at a level of 0.001 mg to 1.99 to 0.5 ml of said organic solvent; and
   introducing said solution containing said corticosteroid into an aqueous medium and forming said nanoparticulate suspension of said pharmaceutically active compound by precipitation and without mechanical shearing under ambient conditions;
   wherein said suspension has a level of surfactant that is less than or equal to 1.0 ppm wherein said nanoparticulate suspension has particles having sizes ranging from 250 nm to 1000 nm, and said suspension is capable of transmitting>85% visible light.

10. A nanoparticulate suspension of a pharmaceutically active compound in a mixture of two solvents comprising:
   pharmaceutically active compound particulate suspended in a liquid mixture comprising an organic solvent and water; wherein said organic solvent has a pKa≥7.0 and consists essentially of the following structure:

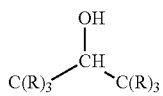

wherein one or more R groups are fluorine atoms and wherein the remaining R groups are selected from the group consisting of a hydrogen atom and an alkyl group; and
      said nanoparticle suspension having particles at a particle size ranging from 250 nm to 1000 nm, said suspension capable of transmitting ≥85% visible light and wherein said suspension has a level of surfactant that is less than or equal to 1.0 ppm.

11. The nanoparticulate suspension of claim 10, wherein said pharmaceutically active compound comprises a corticosteroid.

12. A method for preparing a nanoparticulate suspension of a pharmaceutically active compound comprising:
   combining triamcinolone in hexafluoroisopropanol to provide a solution wherein said pharmaceutically active compound is present at a concentration of 0.001 mg to 1.99 mg to 0.5 ml; and
   introducing said solution into a phosphate buffered saline solution and forming said nanoparticulate suspension of said pharmaceutically active compound by precipitation and without mechanical shearing under ambient conditions;
   wherein said suspension has a level of surfactant that is less than or equal to 1.0 ppm.

13. A method for preparing a nanoparticulate suspension of a pharmaceutically active compound comprising:
   combining a pharmaceutically active compound comprising triamcinolone in hexafluoroisopropanol to provide a solution wherein said pharmaceutically active compound is present at a level of 0.001 mg to 1.99 mg to 0.5 ml and wherein said solvent has a pKa≥7.0; and
   introducing said solution into an aqueous medium comprising hyaluronidase and forming said nanoparticulate suspension of said pharmaceutically active compound by precipitation and without mechanical shearing under ambient conditions;
   wherein said nanoparticulate suspension has particle sizes ranging from 250 nm to 1000 nm and said particle size is formed without mechanical shearing under ambient conditions; and said suspension has a level of surfactant that is less than or equal to 1.0 ppm.

14. The nanoparticulate suspension of claim 10, further comprising, a secondary pharmaceutical compound, wherein said secondary pharmaceutical compound comprises a spreading or diffusing substance.

15. The nanoparticulate suspension of claim 14, wherein said secondary pharmaceutical compound is hyaluronidase.

* * * * *